(12) United States Patent
Van Driessche et al.

(10) Patent No.: US 7,586,017 B2
(45) Date of Patent: Sep. 8, 2009

(54) HYDROGENATION

(75) Inventors: Eddy Theophyle Andrea Van Driessche, Eeklo (BE); Philippe Louis Buess, Overijse (BE); Raphael Frans Caers, Edegem (BE); Arie Van Vliet, Sterrebeek (BE); Ramzi Yanni Saleh, Baton Rouge, LA (US); Jose Manuel Vargas, Prairieville, LA (US); Kenneth Lloyd Riley, Baton Rouge, LA (US); Magdiel Agosto, Greenwell Springs, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 433 days.

(21) Appl. No.: 10/582,742

(22) PCT Filed: Dec. 16, 2004

(86) PCT No.: PCT/EP2004/014479

§ 371 (c)(1),
(2), (4) Date: Feb. 9, 2007

(87) PCT Pub. No.: WO2005/058782

PCT Pub. Date: Jun. 30, 2005

(65) Prior Publication Data

US 2007/0161829 A1  Jul. 12, 2007

Related U.S. Application Data

(60) Provisional application No. 60/530,804, filed on Dec. 18, 2003.

(51) Int. Cl.
C07C 29/141 (2006.01)

(52) U.S. Cl. .................................. 568/882; 568/883

(58) Field of Classification Search ................ 568/882, 568/883
See application file for complete search history.

(56) References Cited

U.S. PATENT DOCUMENTS

| 2,681,374 A | 6/1954 | Bethea .................. 260/683.15 |
|---|---|---|
| 3,188,351 A | 6/1965 | Lemke ........................ 260/604 |
| 3,378,590 A | 4/1968 | Usami et al. ................. 260/598 |
| 3,864,346 A | 2/1975 | Child et al. ............. 260/683.59 |
| 3,868,422 A | 2/1975 | Hart et al. ............. 260/604 HF |
| 4,018,846 A | 4/1977 | Mayer .................... 260/683.59 |
| 4,049,725 A | 9/1977 | Gueant et al. ............ 260/638 B |
| 4,320,237 A | 3/1982 | Kaufhold et al. ............. 568/909 |
| 4,334,118 A | 6/1982 | Manning ..................... 585/529 |
| 4,684,750 A | 8/1987 | Kessen et al. ................ 568/883 |
| 5,324,420 A | 6/1994 | De Munck et al. ........... 208/124 |
| 5,672,800 A | 9/1997 | Mathys et al. ................ 585/520 |
| 5,744,679 A | 4/1998 | Marinangeli et al. ......... 585/526 |
| 6,111,159 A | 8/2000 | Huff et al. ..................... 585/529 |
| 2003/0114718 A1 | 6/2003 | Knoop et al. ................ 568/855 |

FOREIGN PATENT DOCUMENTS

| AU | 200197176 | 6/2002 |
|---|---|---|
| DE | 100 35 120 | 1/2001 |
| DE | 102 27 995 | 9/2003 |
| EP | 0 188 246 | 7/1986 |
| EP | 0 746 538 | 12/1996 |
| EP | 0 808 298 | 6/1998 |
| GB | 643 503 | 9/1950 |
| GB | 2 142 010 | 1/1985 |
| WO | WO 93/16020 | 8/1993 |
| WO | WO 94/29018 | 12/1994 |
| WO | WO 02/094740 | 11/2002 |

OTHER PUBLICATIONS

Cavani et al., entitled "Effect of Water in the Performance of the Solid Phosphoric Acid Catalyst for Alkylation of Benzene to Cumene and for Oligomerization of Propene" Applied Catalysis A: General, Elsevier Science vol. 97, pp. 177-196 (1993), Amsterdam, NL.
"New Syntheses with Carbon Monoxide" by Falbe on p. 17 and 71, New York, 1980.
USSN: U.S. Appl. No. 10/582,929, filed Jun. 13, 2006, Beadle et al., Entitled "Improvements in or Relating to Catalysed Reactions".
USSN: U.S. Appl. No. 10/582,756, filed Jun. 13, 2006, Beadle et al., Entitled "Improvements in or Relating to Hydroformylation".

*Primary Examiner*—Elvis O Price
(74) *Attorney, Agent, or Firm*—Andrew B. Griffis

(57) ABSTRACT

The use of a controlled amount of water in a hydrogenation stage of the oxo process for the production of alcohols which uses at least two reactors in series improves the efficiency of the hydrogenation reaction and catalyst life as does a reduction in the amount of sulphur, chlorine and hydroformylation catalyst residues in the feed to hydrogenation.

47 Claims, 1 Drawing Sheet

HYDROGENATION

CROSS REFERENCE OF RELATED PATENT APPLICATIONS

This application is a National Stage Application of International Application No. PCT/EP2004/014479, filed 16 Dec. 2004, which claims benefit of U.S. Provisional Application No. 60/530,804, filed 18 Dec. 2003. These applications are incorporated herein by reference.

FIELD OF THE INVENTION

The present invention relates to improvements in or relating to the production of alcohols, particularly, but not exclusively, to the production of alcohols containing from 6 to 15 carbon atoms.

BACKGROUND $C_6$ to $C_{15}$ alcohols are produced in large volumes throughout the world by the hydroformylation of olefins to produce aldehydes, followed by hydrogenation of the aldehydes to produce alcohols. The olefins that are used as feeds for the hydroformylation are generally oligomers of olefins that are obtained from petroleum feedstocks. Various processes may be used to produce the olefins used for hydroformylation. For example, the octenes that are used in the production of nonyl alcohol, which is produced in large volumes for the manufacture of plasticiser ester, may be produced by the dimerisation of butenes employing a nickel containing catalyst, e.g. by the Octol® or Dimersol® processes, or dimerisation on a zeolite or other acidic catalyst. These are processes which yield substantially pure octenes. Alternatively olefin mixtures averaging about eight carbon atoms may be obtained by the oligomerisation of olefin mixtures using acid catalysts such as phosphoric acid catalysts.

In both these processes, due to the petroleum origins of the olefins, the olefins typically contain impurities such as sulphur and chlorine which can have a damaging effect on the hydroformylation reaction and, in particular, the hydrogenation reactions. The hydrogenation reactions are performed by catalytic hydrogenation at elevated temperature and pressure and the conditions must be carefully controlled in order to optimise the yield and selectivity of the hydrogenation, ensure safe operation of the hydrogenation unit, secure commercially viable catalyst life and minimize side reactions.

Alternative processes for producing alcohols may comprise the hydroformylation of lower carbon number olefins, such as ethylene, propylene and butenes to the corresponding aldehyde or aldehyde mixtures containing one more carbon number than the starting olefin or olefins. These aldehydes, or mixtures thereof, are then subjected to aldolisation to produce condensation products, typically higher aldehydes containing an extra carbon-carbon double bond, often referred to as enals. These enals or enal mixtures may be hydrogenated to the corresponding saturated aldehydes or aldehyde mixtures, or directly to the corresponding alcohols or alcohol mixtures. Examples of products produced by such processes are 2-methylpentanol, 2-ethylhexanol, 2,4-dimethylheptanol and 2-propylheptanol, but other alcohols and alcohol mixtures produced in this way are also known.

A variety of catalysts have been proposed and used in the hydrogenation of aldehydes to produce alcohols and in certain commercial operations a mixture of catalysts have been used in order to optimize the selectivity of the hydrogenation. For example United Kingdom Patent 2142010 employs a two stage hydrogenation process employing a molybdenum disulphide on carbon catalyst in the first stage and a nickel oxide on Kieselguhr catalyst in the second stage. The process is said to hydrogenate an aldehyde feed containing organosulphur impurities which derive from sulphur impurities in the olefin feed.

Australian Patent Application 200197176 A1 relates to the hydrogenation of aldehydes to produce alcohols and discloses that water should be present in the hydrogenation reactor to hydrolyse formic acid esters, acetals, enol ethers, aldol condensation products and other hydrolysable substances. According to Australian Patent Application 200197176 A1 where a series of hydrogenation reactors connected in series are used, the water may be added before the individual reactors and only the amount required may be added at the beginning in order to prevent formation of a second water phase in the hydrogenation reactor.

It is also known from U.S. Pat. No. 5,324,420 that desulphurisation of the olefin feed to hydroformylation can enhance catalyst life in the production of alcohols especially in the hydrogenation stage.

It is also known that the production of formic acid esters during hydroformylation may be reduced if water is present during the hydroformylation reaction as described in "New Syntheses with Carbon Monoxide" by J. Falbe on page 71. Accordingly water may be injected into the hydroformylation reactor and, in this instance, generally an excess of water is used. Water is therefore often present in the product of hydroformylation.

Following hydroformylation and prior to hydrogenation the product of hydroformylation is subject to catalyst removal and water washing which can also result in the presence of water in the material that is fed to hydrogenation.

DETAILED DESCRIPTION

Figure 1:
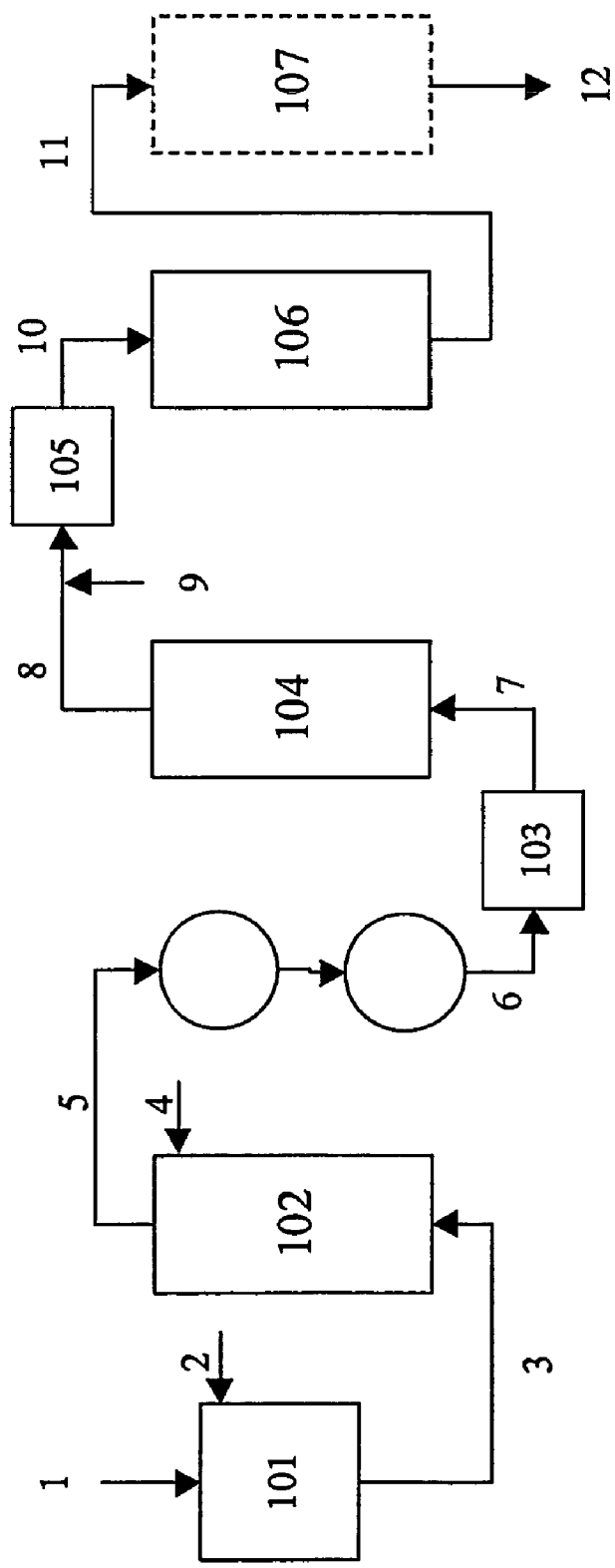
FIG. 1 illustrates a process described herein.

We have found however that free water should not be present during the hydrogenation reaction, particularly if the hydrogenation reaction is performed in the liquid phase. Although the presence of water is beneficial in converting the esters and certain heavy products to the desired alcohols and aldehydes, and in preventing the formation of certain undesired by-products as a result of reactions involving water formation, free water can deactivate the hydrogenation catalyst, particularly when using a cuprous chrome hydrogenation catalyst, which is preferred because it improves the stability of the hydrogenation reaction and provides improved conversion and selectivity. In addition, the presence of a separate water phase under reaction conditions is undesirable. Furthermore, since carbon dioxide is formed during hydrogenation by a mechanism comprising the hydrolysis of the formate esters, any free water present could form carbonic acid with the carbon dioxide, which in turn could corrode the reactors. The water may be introduced into the feed to the second reactor and at this stage the amount of water may exceed the solubility limit providing the amount does not exceed the solubility limit at reaction conditions.

The present invention is therefore concerned with the optimisation of the hydrogenation stage in the production of alcohols in a process that involves hydroformylation followed by hydrogenation.

The present invention therefore provides a process for the production of alcohols comprising the hydroformylation of an olefin or olefin mixture followed by catalytic hydrogenation, wherein the hydrogenation is performed in a series of at least two reactors and water is added to the material discharged from the first reactor that is to be hydrogenated in the second reactor, in an amount such that in the second reactor all the water present is dissolved in the organic phase.

In a preferred embodiment the present invention provides a process for the production of alcohols comprising the hydroformylation of an olefin or olefin mixture followed by catalytic hydrogenation wherein the hydrogenation is performed in a series of at least two reactors wherein water is added to the hydroformylation reactor and no further water is added in the first hydrogenation reactor and water is added to the second hydrogenation reactor.

In this preferred embodiment water will be carried over from the hydroformylation reactor or a demetalling or washing step downstream of the hydroformylation reactor, into the first hydrogenation reactor, the amount of water carried over being such that all the water present is, under reaction conditions, dissolved in the organic phase to be hydrogenated.

In the first hydrogenation reactor a number of side reactions will take place under the hydrogenation conditions. For example formate esters will be hydrolysed to form alcohols, formic acid, carbon monoxide, carbon dioxide, hydrogen, and methanol, and acetals will be hydrolysed to form alcohols and aldehydes. Both of these reactions consume water and accordingly the water is depleted during hydrogenation and further water is preferably added to the material entering the second hydrogenation reactor to optimise the hydrogenation in that reactor. The amount of water added should be such that the total amount of water present in the second reactor is dissolved in the organic phase to be hydrogenated under reaction conditions.

In a further embodiment of the present invention the sulphur content of the material fed to the first hydrogenation reactor is below 10 ppm by weight, preferably below 5 ppm, more preferably below 1 ppm. Sulphur can be present in the product of hydroformylation because of sulphur present in the syngas used in the hydroformylation and particularly because of sulphur present in the olefin that is hydroformylated. Accordingly in a further embodiment of the present invention the olefin used for hydroformylation followed by hydrogenation has a sulphur content below 10 ppm by weight, preferably below 5 ppm, more preferably below 1 ppm, most preferably below 0.1 ppm.

In a further embodiment of the present invention the chlorine content of the material fed to the first hydrogenation reactor is below 10 ppm by weight, preferably below 5 ppm, more preferably below 1 ppm, most preferably below 0.1 ppm. Chlorine can be present because of chlorine present in the catalyst added to the hydroformylation, or because of chlorine present in any other chemical or wash water used in the hydroformylation catalyst removal step and particularly because of chlorine present in the olefin which is the raw material for hydroformylation. Accordingly in a further embodiment of the present invention the chlorine content of the olefin used for hydroformylation followed by hydrogenation has a chlorine content below 10 ppm by weight, preferably below 5 ppm, more preferably below 1 ppm, most preferably below 0.1 ppm.

The present invention therefore further provides an olefin or olefin mixture containing from 5 to 13 carbon atoms useful in the production of alcohols by hydroformylation of the olefin followed by hydrogenation, said olefin containing no more than 10 ppm by weight, preferably no more than 5 ppm, more preferably no more than 1 ppm, most preferably below 0.1 ppm, sulphur and no more than 10 ppm preferably no more than 5 ppm and more preferably no more than 1 ppm, most preferably below 0.1 ppm chlorine. In particular the present invention provides such an olefin having eight carbon atoms useful in the production of $C_9$ alcohols.

It will be understood that such olefin or olefin mixture constitutes a feedstream to be used in commercial hydroformylation operations which are generally large scale and continuous. Such streams may be derived from petrochemical and/or refinery operations such as steam cracking or cat cracking. Typically, they comprise mixtures of olefins that not only have different carbon numbers, but whether or not the carbon numbers are different, comprise linear and branched olefins. Other, non-olefinic, components may be present, for example saturated hydrocarbons.

Whilst the present invention is applicable to any process involving hydroformylation of olefins to produce aldehydes followed by hydrogenation to produce alcohols, it is particularly applicable to the production of $C_6$ to $C_{15}$ alcohols from $C_5$ to $C_{14}$ olefins or olefin mixtures, preferably of $C_8$ to $C_{13}$ alcohols from $C_7$ to $C_{12}$ olefins or olefin mixtures. The invention is especially useful in the production of $C_8$ to $C_{10}$ alcohols from $C_7$ to $C_9$ olefins or olefin mixtures.

The olefin mixtures according to the invention typically comprise not more than 90 wt % of normal or linear olefins, the remainder being branched olefins, typically a mixture of at least 3 isomers with different skeletal structures, preferably at least 5, more preferably at least 8 and most preferably at least 10 isomers with different backbone structures, irrespective of the location of the double bond. The content of normal olefins is readily determined using a capillary gas chromatography (GC) analysis technique, preferably with on-line or in-situ hydrogenation of the feed olefins before they enter the GC column, or more preferably even a combination of the two. This technique involving hydrogenation is also known as "hydro-GC", and in its spectrum all the normal olefins, i.e. the normal alpha olefins and the normal internal olefins combined, show up as one peak per carbon number as the equivalent normal paraffins and which elute typically as the last peak within the same carbon number. The same technique is also capable of separating isomers with different backbone structures, many of which may be identified by calibrating the GC column with model compounds and/or by applying GC-MS. Preferably the content of normal olefins in the olefin mixture is not more than 70 wt %, more preferably not more than 35 wt %, even more preferably not more than 15 wt %, and most preferably not more than 9 wt % of normal or linear olefins. If there are normal paraffins present in the starting olefin mixture, the content thereof may be determined from the equivalent spectrum without the hydrogenation. Usually these are low in the commercial mixtures of interest derived from petrochemical and/or refinery operations from petroleum feedstocks, and if there is too much overlap in the GC spectrum, the amount of normal paraffins present in the starting olefin mixture may be neglected.

The branched olefins subjected to hydroformylation followed by hydrogenation result in branched alcohols; with normal olefins, a certain amount of their derivatives are normal alcohols. When a cobalt catalyst is used in hydroformylation, there will be more normal alcohols produced than when a rhodium catalyst is used, as the cobalt catalyst will tend to move any internal double bond towards an end of the olefin backbone structure before hydroformylating the double bond.

Where the olefin mixture is a mixture of C7 to C9 olefins, the C8 olefin content is preferably at least 50 wt %, more preferably 75 wt %, even more preferably 90 wt %, and most preferably 97 wt %. The carbon number distribution of the olefin mixture may be determined by capillary Gas Chromatography (GC), preferably again by "Hydro-GC", and is again usually expressed in weight %. Standard industry practice is to split the GC spectrum into carbon number regions corresponding to the individual normal paraffins such as n-heptane, n-octane, n-nonane and n-decane. The region eluting before a particular normal paraffin but after the normal paraffin having one less carbon atom than that particular normal paraffin is assigned to the branched paraffins—or branched olefins on a hydro-GC spectrum—having the number of carbon atoms of the particular (higher) normal paraffin. For example, the GC region between n-octane and n-nonane, and the region including the n-nonane, are considered to correspond to all the C9 paraffins, and therefore to the C9 olefins in the starting olefin mixture. Such technique may or may not neglect any paraffins that were present in the olefin mixture, depending on whether an unhydrogenated GC spectrum is obtained in parallel, and on the quality and resolution thereof.

The invention is also particularly applicable to processes in which the hydroformylation is performed at elevated temperatures and pressures using a cobalt or a rhodium catalyst. However, in order to achieve optimum performance in the hydrogenation section it is desirable to remove the cobalt or rhodium species from the product of hydroformylation prior to hydrogenation in the first hydrogenation reactor. When using cobalt, it is preferred that the cobalt level be below 5 ppm, more preferably below 2 ppm. Accordingly in a further preferment of the present invention the product of hydroformylation is treated to remove cobalt species so that the cobalt content is below 1 ppm prior to hydrogenation. When using rhodium, it is preferred that the rhodium level be below 0.1 ppm by weight, more preferably below 50 ppb, even more preferably below 10 ppb, most preferably below 5 ppb by weight.

In another process for the production of C6, C7, C8, C9 and C10 alcohols particularly the $C_6$ alcohol 2-methylpentanol, the $C_7$ alcohol mixture primarily of 2-ethylpentanol and 2-methylhexanol, the $C_8$ alcohols 2-ethylhexanol and/or 2-ethyl-4-methylpentanol, the $C_9$ alcohol 2,4-dimethylheptanol, the $C_{10}$ alcohols 2-propylheptanol and/or 2-propyl-4-methylhexanol, and mixtures thereof, $C_2$, $C_3$ and/or $C_4$ olefins are subject to hydroformylation at low pressure. The aldehyde or aldehyde mixtures produced may then be subject to hydrogenation for producing the corresponding $C_3$, $C_4$ or $C_5$ alcohols, or the aldehydes may be subject to one or more aldol condensation reactions to produce higher and unsaturated aldehydes which are then hydrogenated to produce the desired alcohols or saturated aldehydes. The saturated aldehydes may then be further hydrogenated to the desired alcohols or alcohol mixtures, or they may be oxidised to the corresponding carboxylic acids or acid mixtures. Catalysts used for the hydrogenation of such streams containing saturated or unsaturated aldehydes or enals, may be based on copper, chrome, cobalt, nickel, molybdenum, aluminum oxide, and combinations thereof. Also these hydrogenation reactions benefit from the presence of water by reducing or suppressing alcohol dehydration, formation of hemi-acetals or acetals. A further embodiment of the present invention is therefore to hydrogenate in the liquid phase, saturated or unsaturated aldehydes produced by the low pressure hydroformylation process, which in the case of unsaturated aldehydes is followed by one or more aldolisation steps. The hydrogenation is performed in a series of at least two reactors, and water is added to the material to be hydrogenated in the second reactor in an amount such that the total amount of water present is under reaction conditions dissolved in the organic phase in the second hydrogenation reactor.

The invention further provides apparatus for the operation of the various processes of this invention.

The hydroformylation reaction of the present invention may be performed at elevated temperature and pressure in the presence of a hydroformylation catalyst. The optimum temperature and pressure will depend upon the selection and dosing of the catalyst, the nature of the olefin feed, both in terms of the carbon number(s) of the olefins, the structure of the olefin (linear or branched) and the concentration of the olefin in the feed which is typically a mixture of saturated and unsaturated (predominately olefinic) materials. Typical pressures for the high pressure process are from 50 to 350 barg, preferably 150 to 350 barg, most preferably from 275 to 325 barg. Typical temperatures range from 120 to 190° C., preferably from 165 or 170 to 188° C., e.g. 165 to 185° C., more preferably from 170 to 185° C., e.g. 170 to 180° C., although certain olefin feeds may preferably be hydroformylated at lower temperatures such as from 100 or 120 to 140° C. typically for reasons of olefin reactivity or reaction selectivity. The catalyst used in the high pressure hydroformylation is usually a cobalt or a rhodium catalyst and generally the active cobalt catalyst is hydr(id)ocobalt(tri- or tetra-)carbonyl and cobalt concentrations of up to 0.8 wt % cobalt on the olefin content of the feed are used, preferably from 0.01 or 0.1 wt % to 0.5 wt % cobalt. Using rhodium under such high pressures, much lower concentrations may be used, such as 0.1 to 200 ppm by weight relative to the olefin feed, preferably 0.2 to 50 ppm, more preferably 0.3 to 20 ppm, even more preferably 0.4 to 5 ppm by weight. Also the temperatures may be lower when using rhodium, using the benefit of its higher activity compared to cobalt, and may be 10, 20, 30 or even 40° C. lower than those when using cobalt.

Hydroformylation reactions of lower olefins such as ethylene, propylene and butenes have generally employed rhodium catalyst, stabilised by phosphorus-containing ligands and operated in what is known as the low pressure oxo technology, originally developed by Union Carbide Corporation and currently available under licence from Davy Process Technology Ltd. The hydroformylation is preferably carried out in the presence of a rhodium catalyst complex in conjunction with an organophosphorus ligand. This organophosphorus ligand may be a tertiary organophosphine or an organophosphite. The triorganophosphine ligand can be a trialkylphosphine such as tributylphosphine, a C1-C6 alkyldiarylphosphine such as butyldiphenylphosphine, an aryldialkylphosphine such as phenyl-dibutylphosphine, an aryldialkyl diphosphine such as cyclohexyldiphenyl phoshine, tetraphenyldiphosphino-methane, 1,2-bis(diphenyl phosphino) ethane, 1,3-bis(diphenyl phosphino) propane, 1,4-bis (diphenyl phosphino) butane, and the bisphosphine ligands described in EP-A 279,018, EP-A 311,619, WO 90/06810 and EP-A 71,281. However particular phosphines such as triphenylphosphine, tri-p-tolylphosphine, trinaphthylphosphine, phenyldinaphthylphosphine, diphenylnaphthylphosphine, tri(p-methoxyphenyl)-phosphine, tri(p-cyanophenyl) phosphine, tri(p-nitrophenyl)phosphine, pN,N-dimethylaminophenylbisphenyl-phosphine and the like are preferred. Triphenylphosphine is most preferred.

The phosphine may also be made water soluble, by providing it with one or more ionic functions. Examples of such phosphines are triphenylphosphine monosulfonate (TPPMS) or triphenylphosphine trisulphonate (TPPTS), but many other ionic ligands are known.

Organophosphite ligands that can be used are disclosed in U.S. Pat. No. 4,599,206, U.S. Pat. No. 4,668,651, U.S. Pat.

No. 4,737,588, U.S. Pat. No. 4,748,261, U.S. Pat. No. 4,769,498, U.S. Pat. No. 4,774,361, U.S. Pat. No. 4,789,753, U.S. Pat. No. 4,835,299, U.S. Pat. No. 4,871,880, U.S. Pat. No. 4,885,401, U.S. Pat. No. 5,179,055, U.S. Pat. No. 5,288,918, U.S. Pat. No. 5,312,996, U.S. Pat. No. 5,364,950, U.S. Pat. No. 5,681,473, U.S. Pat. No. 5,756,855, WO 97/20793. Preferred is 6,6'-[[3,3',5,5'-tetrakis(1,1-dimethylethyl)-1,1'-biphenyl]-2,2'-diyl] bis(oxy)] bis-dibenzo[d,f][1,3,2]-dioxaphosphepin, or 6,6'-[[3,3',5,5'-tetrakis(1,1-dimethylpropyl)-1,1'-biphenyl]-2,2'-diyl] bis(oxy)] bis-dibenzo[d,f][1,3,2]-dioxaphosphepin, or 6,6'-[[3,3'-bis (1,1-dimethylethyl)-5,5'-dimethoxy [1,1'-biphenyl]-2,2'-diyl] bis(oxy)] bis-dibenzo[d,f][1,3,2]-dioxaphosphepin, or tris(2,4,6-di-t-butylphenyl)-phosphite. Most preferred is 6,6'-[[3,3',5,5'-tetrakis(1,1-dimethylethyl) 1,1'-biphenyl]-2,2'-diyl] bis (oxy)] bis-dibenzo[d,f][1,3,2]-dioxaphosphepin. Ionic varieties of such phosphites are disclosed in U.S. Pat. No. 5,059,710 and U.S. Pat. No. 5,113,022.

The low pressure hydroformylation process may be carried out in a manner known by the persons skilled in the art, for example by the process according to U.S. Pat. No. 4,247,486, U.S. Pat. No. 4,287,370, U.S. Pat. No. 5,053,551, U.S. Pat. No. 6,100,432, WO 02/00582, DE 10128325, WO 97/20792, WO 97/20793, WO 97/20794, WO 97/20795, WO 97/20796, WO 97/20797, WO 97/20798, WO 97/20799, WO 97/20800 and WO 97/20801. Further variations and improvements on ligands, the hydroformylation process and/or the treatment of the hydroformylation medium have been disclosed in U.S. Pat. No. 5,731,472, U.S. Pat. No. 5,741,942, U.S. Pat. No. 5,741,943, U.S. Pat. No. 5,741,945, U.S. Pat. No. 5,786,517, U.S. Pat. No. 5,763,670, U.S. Pat. No. 5,763,671, U.S. Pat. No. 5,763,677, U.S. Pat. No. 5,763,679, U.S. Pat. No. 5,763,680, U.S. Pat. No. 5,767,321, U.S. Pat. No. 5,789,625, U.S. Pat. No. 5,728,893, U.S. Pat. No. 5,886,237, U.S. Pat. No. 5,741,944, U.S. Pat. No. 5,731,473, U.S. Pat. No. 5,744,650, U.S. Pat. No. 5,874,639, U.S. Pat. No. 5,874,640, U.S. Pat. No. 5,892,119, U.S. Pat. No. 5,886,235, U.S. Pat. No. 5,917,095, U.S. Pat. No. 5,952,530, U.S. Pat. No. 6,090,987, U.S. Pat. No. 6,252,121, U.S. Pat. No. 6,307,109, and U.S. Pat. No. 6,294,700.

Liquid phase processes for hydrogenating the C3 to C5 aldehydes produced by these low pressure rhodium based hydroformylation processes, or for hydrogenating the C6 to C10 enals or enal mixtures produced by aldolisation of one or more of said C3 to C5 aldehydes, are disclosed in U.S. Pat. No. 4,960,960 or U.S. Pat. No. 5,093,535. These processes include the operation of reactors in series, either as a series of catalyst beds in the same reactor vessel, or as catalyst beds in separate reactor vessels.

The hydroformylation catalyst for the high pressure process may be supplied already absorbed in the olefin feed and/or as fresh catalyst. It is preferably supplied absorbed in the olefin feed. In the case of cobalt, the initial cobalt species can be dicobalt octacarbonyl Co2 (CO)8, a salt of cobalt with an acid, e.g. cobalt sulfate or carbonate, and preferably with an organic acid, like formic acid or acetic acid, but also salts with higher molecular weight acids like oleic, stearic, or naphthenic acids are known. It can also be cobalt oxide or hydroxide. This cobalt source may be preformed in a separate reactor in order to convert it to the carbonyl form, or this conversion may occur in the hydroformylation reactor itself. Under the hydroformylation conditions, an equilibrium is believed to exist between two cobaltcarbonyls:

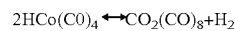

$$2HCo(CO)_4 \leftrightarrow Co_2(CO)_8 + H_2$$

Hydr(id)ocobalt(tetra)carbonyl (HCo(CO)$_4$) is generally believed to be the active catalyst form or at least the precursor to the active catalyst form, which also may be HCo(CO)3. The higher the hydrogen partial pressure in the hydroformylation reaction and the higher the temperature the greater the concentration of hydrocobalt carbonyl, and hence the greater the reaction rate.

Dicobaltoctacarbonyl, under influence of higher temperature and/or lower partial pressures of carbon monoxide, may split off one or more carbon monoxide molecules and form cluster compounds that gradually contain more cobalt and less carbonyl functions, and which are less and less soluble in the reaction medium, up to the point where the cobalt comes out of solution in forms that contain little carbon monoxide and approach the state of cobalt metal or are metallic. This phenomenon is referred to as "cobalt plating". These clusters and lower carbonyl containing forms of cobalt are inactive for the hydroformylation reaction. It is well known that at a given temperature and cobalt concentration, a certain partial pressure of carbon monoxide is required in order to maintain the stability of the cobaltcarbonyls and to prevent the cobalt coming out of solution and depositing on the inside of the equipment. Consequently, the concentration and the stability of the active hydroformylation catalyst is, under constant operating conditions, affected by the gas composition, e.g. the levels of inerts and those of H2 and carbon monoxide.

The hydroformylation reaction is highly exothermal and the reaction is typically fast. The heat given off and the rate of heat release to some extent depend upon the nature and structure of the olefin that is being subject to hydroformylation. In general the less branched the olefin the more reactive it tends to be and with branched olefins the reactivity depends on the location of the double bond in relation to the branches. Olefins in which the double bond is located between two branches have, for example, a low reactivity.

The rate of reaction has a substantially exponential relationship to the temperature of the reaction.

It is therefore also important that the conditions of the hydroformylation reaction are controlled to minimize fluctuations in the reaction temperature which can cause variations in the product formed and plating out of cobalt metal from the catalyst when using the preferred cobalt catalysed hydroformylation. Control is also important for safety purposes to prevent reaction runaway. Accordingly, in addition to optimizing gas utilization, careful management of the gas profile according to our copending U.S. patent application 60/530,805 filed 18 Dec. 2003 helps to optimize the reaction temperature with the beneficial effects of increasing reaction yield and minimizing or eliminating the plating out of the cobalt within the reactor which can occur if the reaction temperature is too high. In this case, extensive cleaning is required with for example nitric acid, requiring that the reactor be taken out of service.

In a preferred aspect of the present invention hydroformylation takes place in a series of reactors and the composition of the materials fed to the second and any subsequent hydroformylation reactors is controlled by recycle of product gasses according to our copending U.S. patent application 60/530,805 filed 18 Dec. 2003. Use of this preferred technology aids control of the gas compositions and the temperatures that are created in the reactors. These techniques therefore lead to higher conversion, higher yields and higher selectivity under constant and safe conditions.

When using a cobalt catalyst, the ratio of hydrogen to carbon monoxide in the fresh syngas is typically about 1.3:1 since at this ratio the plating out of the cobalt is substantially avoided, or sufficiently low to be acceptable. However, when using a series of reactors for hydroformylation due to the reaction in the first reactor where there is some conversion of olefins to aldehydes and alcohols there will be a change in the ratio of hydrogen to carbon monoxide. This change will depend on the degree of conversion to alcohol or aldehyde since the conversion to alcohol requires twice as much hydrogen as is used in the formation of an aldehyde. Accordingly, it may be necessary to replenish the hydrogen level in the second and perhaps subsequent reactors (if used) and this can be accomplished by balancing the composition of the recycle gasses and/or by introducing unreacted gasses from the downstream hydrogenation reactor used to convert aldehydes in the final product of hydroformylation into alcohols. Such recycle is described in our above-mentioned copending patent application. When linear olefins are being processed a lower ratio of hydrogen to carbon monoxide in the first reactor such as 1:1 or 1.1:1 may be preferred. However, irrespective of the preferred ratio, it needs to be controlled.

Ideal syngas compositions, expressed as mole ratio of hydrogen to carbon monoxide, are not always available. For example, where the ideal composition may be at a 1.3 ratio, the gas may have a higher hydrogen content such as a ratio of 1.5. As hydrogen and carbon monoxide are reacted away from this gas in roughly equal portions in the initial stages of the Oxo reaction, the hydrogen to CO ratio will continue to increase. In such a case, the minimum partial pressure requirements for CO are met by using more excess fresh gas and avoiding the recycle of any gas containing less CO than the minimum requirement. The reactor operating temperature may also be reduced to compensate for the higher reactivity and the higher propensity for cobalt carbonyl to become unstable.

Syngas may be available at a composition less rich in hydrogen than desired, say at a ratio of 0.8. In this case, economy of syngas utilization is achieved by recycling hydrogen depleted gas from downstream stages and supplementing it with hydrogen, from an external source, to various stages of the Oxo reactor sequence, as described in our above-mentioned copending patent application.

In a preferred embodiment to ensure high olefin conversion the reaction system comprises a series of at least three hydroformylation reactors and, for the reasons discussed above in relation to the second reactor, it is preferred that a hydrogen rich gas, composed of optionally fresh syngas and recycle gas from the hydroformylation reaction and/or from the downstream hydrogenation section, is fed to the third reactor together with the reaction product from the second reactor.

In a further preferred embodiment the reactor system includes a fourth reactor in which the final, say up to 5% conversion of the olefin takes place. In other embodiments, there may be up to 6 reactors. Optionally, part of the recycle gasses and/or a gas rich in hydrogen may be added to the feed of the fourth and/or subsequent reactors.

The hydroformylation reactors used in the present invention are continuous reactors which are preferably gas-lift reactors and, more preferably are loop reactors such as those described in U.S. Pat. No. 4,320,237, U.S. Pat. No. 3,830,846, WO 01/14297, GB 1,308,206 and U.S. Pat. No. 4,312,837 and WO 94/129018. The reactors are provided with cooling coils, heat exchangers, and/or jackets for temperature control and it is preferred that the materials be introduced at the bottom of the reactors and are taken off primarily at the top of the reactors whilst the material not taken off, is recycled around the internal or external reactor loop. Accordingly syngas, olefin potentially containing dissolved or entrained cobalt, water or a hydrocarbon stream containing cobalt, and recycle gas is fed to the bottom of the first reactor. The reaction product is taken off at the top of the first reactor and is then fed to the bottom of a second reactor where it is mixed with fresh olefin and fresh syngas. The reaction product is then taken off at the top of the second reactor. In a preferred reaction system the reaction product from the second reactor is fed to the bottom of a third reactor where it is mixed with fresh syngas and recycle gas. This reaction product is then taken off at the top of the third reactor. In a further embodiment the product from the third reactor is then fed to the bottom of a fourth reactor and the final hydroformylation reaction product taken off at the top of the fourth reactor. All reactors in the series can be gas-lift reactors, or loop reactors. If not, only the reactors in the first position and optionally those in second and/or third position may be gas-lift or loop reactors, and the remainder may be vertical tubular reactors as explained above. If a separate water stream is fed to any of the reactors, typically the first of the series, a two-phase water/organic stream may be removed from the bottom of that reactor, and optionally fed through to a point downstream in the flowscheme, preferably a hydroformylation reactor situated downstream, as is illustrated in WO 01/14297.

After passing through the series of reactors the final product of the hydroformylation reaction comprises a mixture of alcohols, aldehydes, unreacted olefins, paraffins, formate esters, heavy oxo fraction comprising dimer and higher condensation products such as ethers, esters, acetals, hemi-acetals, ether aldehydes and ether alcohols. The mixture will also contain hydrogen, carbon monoxide, generally catalyst residues and inert materials. The product must therefore be purified and separated into its components.

The purification involves the removal of dissolved and entrained catalyst species which may be recycled for further use. In the high pressure hydroformylation process, the reaction product is typically a gas liquid mixture at about 175° C. and 275 bar gauge pressure and due to the high pressure certain normally gaseous materials are dissolved or are entrained in the liquid phase. The first step in the purification may be the removal of catalyst residues, such as cobalt, and the preferred method for cobalt removal may be by injection of a hot dilute base such as caustic soda and/or sodium (bi-)carbonate into the reaction product in a decobalter vessel following the final hydroformylation reactor. Preferably in this case, the reaction product from the final reactor is fed to the bottom of the decobalter which is conveniently a long vertical jacketed pipe. In the decobalter the majority of the cobalt is converted into NaCo(CO)4, the water soluble sodium salt of hydrocobaltcarbonyl. If sodium (bi-)carbonate is used or carbon dioxide is present, a small portion of the cobalt may be converted into solid cobalt carbonate. In the absence of carbon dioxide or sodium carbonate, cobalt may be converted to solid cobalt hydroxide, $Co(OH)_2$. We have found that the decobalting is more effective if the caustic soda and/or carbonate and the reaction product from the final hydroformylation reactor are introduced into the decobalter in a manner that avoids intensive mixing of the products—we have found that if the oil phase (reaction product) and the water phase (dilute caustic soda) are brought into contact gradually, less cobalt is lost as more of it is converted into the water soluble sodium salt. The reaction product of hydroformylation and the dilute base are therefore introduced through separate injection nozzles at least one of which has a tapered opening to allow the material to mix only gradually and with minimal turbulence with the stream of the other material. Minimizing the turbulence also minimizes the dip in partial pressure of carbon monoxide at the injection point, which minimizes the cobalt plating at that point. We have found that the use of a tapered diffuser-type opening for the injection of the reaction product of from 2 to 10°, preferably 4 to 8°, most preferably 6° to the vertical is particularly useful.

The decobalter conditions are such that the neutralization converts the hydrocobalt carbonyl to sodium cobalt carbonyl. In this way the presence of cobalt in the waste water can be avoided. Preferred conditions are to use a stoichiometric excess of sodium hydroxide or carbonate above the amount needed for cobalt neutralization, an excess of 100 to 200% particularly 140 to 180% is useful. The decobalter is typically operated at a temperature in the range 125-165° C. and it is preferred that sufficient carbon dioxide and/or carbonate is present in the decobalter to ensure the formation of sodium cobalt carbonyl and to also buffer the pH in the range 7.8 to 8.5. Further possible embodiments can be found in U.S. Pat. No. 5,130,107.

Alternative to this alkaline decobalting method at high pressures, the cobalt may be removed by an acidic and/or oxidative method as described in J. Falbe, in WO 01/14297, in U.S. Pat. No. 4,625,067, U.S. Pat. No. 5,130,107, U.S. Pat. No. 5,235,112, U.S. Pat. No. 5,237,104, U.S. Pat. No. 5,237,105, U.S. Pat. No. 5,321,168, U.S. Pat. No. 5,354,908, U.S. Pat. No. 5,410,090, U.S. Pat. No. 5,457,240, FR 1089983, EP 642488, EP 643683, WO 03/082788 and WO 03/082789. Some of these processes do the catalyst removal from the hydroformylation product at conditions close to the pressures and temperature used in hydroformylation, others may do it at a less severe conditions, being a lower temperature and/or pressure, typically after separating at least a portion of the gasses that are contained in the hydroformylation product. The acidic methods typically apply low molecular organic acids, like formic acid and/or acetic acid. They may additionally involve a stripping step, wherein part of the cobalt in a volatile form like H Co (CO)4 is stripped using a gas from the liquid hydroformylation product, and carried into an absorber where it may be absorbed into a suitable liquid like feed olefin or heavy byproducts. The oxidative methods may involve the use of oxygen or an oxygen containing gas, or air. The methods may convert all or only a portion of the cobalt values to their zero valency and/or to their +2 valency equivalents. Part or all of the cobalt values may be converted to cobalt salts, preferably a salt that is soluble in water, more preferably a salt from an organic acid like cobalt formate or acetate. The cobalt values may be fed or recycled to the hydroformylation reaction in a form dissolved in organic liquid such as olefin feed, heavy byproducts or another suitable liquid, in the form of a carbonyl or as a salt, which may be water or oil soluble, and may be formate, acetate, oleate, naphthenate of any other suitable carboxylate dissolved in a suitable organic carrier or in water.

Following decobalting the decobalted product, which comprises dissolved gas, entrained gas, water and the hydroformylation product mixture, may be fed, possibly after cooling, to a high pressure separator which separates the free gas as high pressure offgas from the liquid phase. Typically, the high pressure separator operates at a pressure of 250 barg or higher, preferred pressure is in the range 250 to 300 barg with 260 to 270 barg being most preferred. In another variety, the hydroformylation pressure may be not more than 210 barg and the high pressure separator may be at a pressure of 20-30 bar below that. The gas is separated off and where gas recycle is used the amount required for recycle is sent to an offgas recycle compressor system. Any excess gas may be disposed of. In addition, unwanted gasses such as excess nitrogen and other inerts may also be removed to ensure that the recycle of gasses does not result in an undesirable build up of inert gasses such as nitrogen in the hydroformylation reactors.

The liquid left in the high pressure separator may then be fed to an intermediate pressure separator where the pressure is reduced to a level that a major portion of the gasses still dissolved or entrained in the liquid from the high pressure separator are released as intermediate pressure offgas. In certain processes it may be useful to employ more than one high pressure separator in which case two intermediate pressure separators may be employed or the liquid products from the high pressure separators may be combined and fed to a single intermediate pressure separator. Here again, any excess gas may be disposed of and unwanted gasses such as methane may be removed to ensure that a recycle of gasses does not result in an undesirable build up of methane.

The pressure in the intermediate pressure separator is typically between 50 and 200 barg, preferably between 80 and 130 or 150 barg, preferably between 90 and 110 barg and we have found that 100 barg is particularly useful. The reduction in the pressure releases the dissolved gasses, particularly unreacted hydrogen and carbon monoxide, and methane, of which a portion can be sent to the offgas recycle compressor system for subsequent recycle. The rest is then typically disposed off as a purge stream. Accordingly, offgas from both the high pressure separator and the intermediate pressure separator can be combined in the offgas recycle compressor system to produce the recycle materials when employed. The flows to the recycle compressor and the purge flows from high and intermediate pressure separators may be used to adjust the balance of the gasses, particularly the balance of hydrogen, carbon monoxide, carbon dioxide, nitrogen and methane that are fed to the hydroformylation reactors for the catalysed hydroformylation reaction with the olefin. Optionally the hydrogen content in hydroformylation may be adjusted by the incorporation of hydrogen offgas from the hydrogenation unit of the present invention.

When the offgasses from the high pressure and intermediate pressure separators, optionally together with a hydrogen stream from the downstream hydrogenation reactor, are recycled, they may be fed to the recycle compressors and, if necessary, fresh hydrogen may be added to produce the stream for hydroformylation having the desired composition. It is preferred that the recycle compressor system comprises a series of gas compressors or compressor stages in which the gas pressure is gradually increased to the pressure required in the hydroformylation reaction. We particularly prefer to use a recycle compressor system comprising three gas compressors or compressor stages in series. In such a system the offgas from the high pressure separator and the intermediate pressure separator may be fed to the first compressor which typically operates at a pressure between 50 and 60 barg. Hydrogen as the offgas from the hydrogenation reactor (which typically also contains carbon dioxide, some carbon monoxide, plus nitrogen and methane) may also be fed to the first compressor. The gas mixture formed in this first compressor may then be fed to a second compressor where the pressure may be increased to within the range 140 to 180 barg, preferably 150 to 170 barg and we have found that 160 barg is particularly convenient. The product of the second compressor may then be passed to the third compressor and additional gas from the high pressure separator may be introduced to ensure the desired composition of the recycle gas feed to the first and second hydroformylation reactors. The pressure is then raised in the third compressor and the product from the third compressor fed to the first and second hydroformylation reactors along with the olefin feed, hydroformylation catalyst and fresh gasses.

The effective operation of the hydroformylation reaction therefore depends upon optimizing the combination of physical conditions such as temperatures, pressures, feed rates of raw materials, space velocity in the reactors and the chemical process conditions. The chemical conditions include in each of the reactors the nature of the olefin feed, relative proportions of olefin feed and other gasses including hydrogen, carbon monoxide and inerts such as nitrogen, methane and carbon dioxide as well as catalyst concentration. The amount of offgas that should be recycled and the amount of syngas and olefin that should be fed to the second and, optionally, subsequent reactors depends on many of these variables. However by establishing the offgas pressure from the high pressure separator and monitoring the composition of the offgas, which includes hydrogen, carbon monoxide and the various inerts, the hydrogen and carbon monoxide partial pressures at the end of the hydroformylation reaction can be calculated and used to control the gas compositions in the upstream hydroformylation reactors. High hydrogen and carbon monoxide partial pressures enhance the stability of the cobalt catalyst, and high hydrogen partial pressures assure a favorable hydroformylation reaction rate. These desires are in conflict with the desire for a higher level of inert buildup, which enables more effective gas purging and improved overall gas utilization, because less valuable hydrogen and carbon monoxide need to be purged with the inerts. This must however be balanced with the constraints imposed by a fixed equipment design pressure, which can result in a lower hydrogen and carbon monoxide content of the high pressure offgas and hence also in hydroformylation. The optimal control point therefore is a compromise between these counteracting preferences. Since the consumption of hydrogen in hydroformylation is greater than the consumption of carbon monoxide, where a series of hydroformylation reactors is used, hydrogen will be depleted relative to carbon monoxide in the first reactor. This difficulty can be overcome by increasing the proportion of hydrogen in the recycle gas that is fed to the second and/or a subsequent hydroformylation reactor.

As a general guide we have found that the pressure at the end of the hydroformylation reaction should be kept above 170 barg, preferably above 190 or 200 barg, more preferably above 210 or 220 barg, most preferably above 240 barg in order to avoid cobalt plating in the hydroformylation reactors. We have also found that the carbon monoxide content of the offgas from the high pressure separator should be such that the partial pressure of CO is above 75 barg, better above 77 barg, preferably above 84 barg, since if the partial pressure drops below these levels cobalt plating may occur in the hydroformylation reactors. Similarly the hydrogen content of the offgas from the high pressure separator should be such that the partial pressure of hydrogen is above 75 barg, better above 77 barg, preferably above 84 and more preferably above 91 barg, since if the partial pressure drops below this level there is a drop in reaction rate. These issues may be controlled by checking the syngas composition, the pressure drop across the hydroformylation reaction and the proportion of inerts in the various streams and making the appropriate adjustments. The use of at least two reactors in series and the separate adjustment of the feeds to the reactors by the recycle of gasses can make a significant contribution to the efficiency and effective operation of the hydroformylation reaction.

Another important aspect of the hydroformylation reaction is the reaction temperature and temperature control. The reaction is highly exothermic and the temperature generated depends on the reactivity of the olefins and the concentration and ratio of the reactive materials, the catalyst concentration and the volume of inert material present. Accordingly the recycle gasses can be used to adjust the amount and ratios of the reactive materials present and the composition of the recycle gasses can be adjusted as a component of reaction temperature control. The reactors are also provided with cooling systems. These can be internal cooling coils or piping, or a jacket around the reactor, or a heat exchanger that is made part of the reactor, such as is disclosed in WO 01/29018. A combination of these cooling means may be employed. A heat exchanger which is part of a loop reactor is typically located in the downward leg of the loop, preferably in the lower part of the leg, and is often known as a conditioner. The rate of heat transfer from the reacting fluid to the wall of any of such cooling system, and hence the reactor cooling, is improved when the reacting fluid has a higher velocity relative to the wall of the cooling system.

In the preferred use of loop reactors, the circulation in the loop reactor is important for the control of the degree of mixing of the reactants and for an even temperature distribution. We have found that in order to obtain a well mixed reaction mixture the rate of circulation within the loop should be at least six times the rate of feed of materials to the reactor. We have also found that a temperature difference between the reactor outlet temperature and the conditioner inlet temperature of greater than 20° C. can indicate insufficient circulation. Preferably this temperature difference is lower than 20° C., such as not more than 16 or even 110° C., preferably not more than 5° C., however the preferred difference depends on the reactivity of the olefins being hydroformylated and on the other operating conditions.

Cooling water or another medium such as an alkanol, for example methanol, is provided to the cooling system, if present. Such cooling system may comprise a jacket and a conditioner, for each reactor. The flow rate of the cooling water or medium is preferably substantially constant and high, in order to enhance heat transfer, so the cooling system may comprise a pumparound setup for circulation over the jacket and/or the conditioner. In a loop reactor, the cooling water circulation is preferably in countercurrent with the process fluid flow. Hot water liquid or vapor may be removed from this system and colder water may be introduced into it. The colder water flow rate will be selected according to the size of the reactor and the calculated heat generated by the reactor. For reactions to be performed in the temperature range of 170° C. to 190° C. we prefer that the cooling water has a temperature in the range of 140-170° C., and the colder water introduced may have a temperature of 90 or 100 to 125° C. If the feed olefin is low in reactivity, for instance because it is of a high carbon number, the cooling system may be utilised to supply heat into the reacting fluid.

In order to improve the selectivity of the hydroformylation reaction, water may be present in the hydroformylation reactors. We have found that the injection of water reduces the formation of formate esters and heavy by-products. When used, water should be injected into the first reactor, and may also be injected into the second and subsequent reactors, if they are used, but we have found that this is not always essential. In a gas-lift reactor, the formation of a significant volume of a stagnant free water phase in the bottom can become an impediment or even an obstruction to the circulation of the reactor fluid. Gas-lift reactors from which any free water is continuously removed from the bottom have been described in WO 01/14297. If there is no water removal capability, the quantity of water that is introduced should preferably not exceed or not exceed by more than 10 or 20% the solubility of the water in the reaction mixture, to avoid the formation of a stagnant free water phase in the reactor. We have found that no more than 2 wt % of water based on the weight of olefin feed should be used in the first reactor and typically from 1.0 wt % to 1.75 wt % particularly 1.5 wt % should be used. The weight of the olefin feed being the weight of unsaturated materials in the feed which is typically above 95 wt % of the feed and frequently about 99 wt % of the feed.

Where water is injected into the second reactor, similar considerations may apply depending on the design of the reactor. Due to the different liquid composition in the second reactor, the water solubility may be different in this reactor, and we prefer to use typically a total of 2.5 wt % water present based on the olefin feed. It needs to be understood that these water levels depend on the olefin type and alcohol product that is processed, due to the different water solubility of the corresponding process streams. It also needs to be understood that the distribution of the water injected depends on the size of the individual reactor stages.

We have found that the injection of water provides a significant improvement in plant utilization as well as carbon monoxide utilization. The water should be injected in a manner that ensures good mixing of the water with the reactants and also prevents large fluctuations in the olefin to water feed ratios.

Accordingly, it is preferred that the water be injected into a fully operational reactor and when a loop reactor is used it is preferred that the materials are circulating at a velocity of at least 0.6 meters/sec when the water is injected. It is also preferred that the water and the olefin are continuously introduced into the reactor at the desired water to olefin ratio.

The present invention is applicable to processes which employ any liquid phase catalytic hydrogenation technique. Many of those employ heterogeneous catalysts, in fixed bed reactors or in slurry circulating reactor systems. They may use any of the conventionally used supported metal catalysts, such as Ni, Pd, or Pt supported on a variety of supports such as granular carbon, silica, silica-alumina, zirconia, silicon carbide, or copper chromite. Other useful catalysts include cobalt compounds; nickel compounds which may contain small amounts of chromium or another promotor; mixtures of copper and nickel and/or chromium; and other Group VIII metal catalysts, such as Pt, Pd, Rh and mixtures thereof, on supports, such as carbon, silica, alumina or silica-alumina. The nickel compounds are generally deposited on support materials such as alumina or kiezelguhr. For example nickel based catalysts may be used such as supported nickel sulphide catalyst. The process may also involve the use of different, catalysts in the series of hydrogenation reactors as is described in U.S. Pat. No. 5,324,420. Other suitable catalysts and processes are disclosed in U.S. Pat. No. 4,982,011, U.S. Pat. No. 4,647,707, U.S. Pat. No. 4,658,068, U.S. Pat. No. 5,059,718, U.S. Pat. No. 5,306,848, U.S. Pat. No. 5,324,420, U.S. Pat. No. 5,382,715, U.S. Pat. No. 5,399,793, U.S. Pat. No. 5,663,388, U.S. Pat. No. 5,877,358, which uses intermediate product recycle, or U.S. Pat. No. 6,278,030.

However, we prefer to use a cuprous chrome hydrogenation catalyst and particularly a catalyst containing from about 20% to 40% by weight of each of copper and chromium, based on the weight of the total catalyst including any support, preferably from 25% to 32% of each of copper and chromium, more preferably 29% to 31% of each of copper and chromium. The remainder is typically barium, silica and carbon by way of binders and supports. They may contain up to 10 wt % silica. Preferred catalysts comprise G 22 RS available from Süd-Chemie and Cu 1155 T available from Engelhard. Cuprous chrome catalysts are preferred because they have a low tendency to cause reaction runaways.

Many of the hydrogenation catalysts, such as cuprous chrome, are poisoned by sulphur species. Desulphurisation may be performed optionally on the olefin feed to the hydroformylation, with techniques known in the art, or as disclosed in U.S. Pat. No. 5,324,420, which uses a massive nickel catalyst containing some alumina and silicium. However, the presence of silicium together with alumina can cause this catalyst to show acidity, and therefore to cause olefin dimerisation. For certain of the olefin feeds, these dimers formed in desulfurisation cause hydrocarbons to show up in the product alcohol after hydroformylation, hydrogenation and distillation. It is therefore important to use desulphurisation catalysts with a low acidity level. This can be achieved by having either a high aluminium/silicium ratio, approaching pure aluminium as the support, or with a very low aluminium/silicium ratio, approaching a pure silica support.

In another embodiment of the current invention, we prefer to use heterogeneous catalysts that are not poisoned by any sulphur species that may be present in the feed to hydrogenation. This provides a more simple process for producing alcohols, because it avoids the need to remove sulphur compounds from the olefin feed or from the synthesis gas feed to the hydroformylation reaction, or from the hydroformylation product. Suitable catalysts whose activity is not destroyed by sulphur impurities, may be monometallic catalyst compositions such as sulphided Mo oxide supported on carbon. Further examples are bimetallic catalyst compositions, such as sulphided Co oxide/Mo oxide supported on alumina, or sulphided Ni oxide/Mo oxide supported on alumina. We have also found that reduced or partially reduced sulphided Ni/Mo or Co/Mo, supported on alumina, is tolerant to sulfur in the hydrogenation feed, unlike reduced nickel supported on alumina. Reference is made here to a copending application U.S. Ser. No. 60/504,543, filed on Sep. 19, 2003. However, we have found that catalyst compositions which comprise one or more active metals on acidic supports can demonstrate excessive by-product formation when used for the hydrogenation of aldehydes. Such acidic supports may be alumina ($Al_2O_3$), silica-alumina, or carbonaceous supports that may be treated to make them acidic.

It is a further embodiment of our invention that these supports can be modified to reduce their acidity under process conditions. When used, the modifiers are materials of a basic nature, i.e. are providing basicity, under process conditions, thereby reducing overall substrate acidity by counteracting the acidity inherent to the support without the modifier. The modifiers may be any of the members of Group IA or IIA of the Periodic Table of the Elements. In particular, compounds that may be used can be magnesium compounds or components thereof, but calcium, sodium and potassium may be used as well. These modifiers are typically added as fully oxidized material during catalyst formulation. An alternative for reducing the acidity of the catalyst support during operation is by adding a small amount of base to the feed to be hydrogenated, similar to what is disclosed in WO 01/87809 [English equivalent US 2003/0114720 A1].

An alternative process for hydrogenating aldehyde containing streams to corresponding alcohols according to the present invention uses bi-phasic catalysis involving ionic liquids as a separate liquid phase. Ionic liquids are non-coordinating solvents for a wide range of transition metal catalysts. They are immiscible with a number of organic solvents and hydrocarbons, and therefore provide a suitable environment to carry out bi-phasic catalysis. Examples of suitable ionic liquids may be the following combinations:

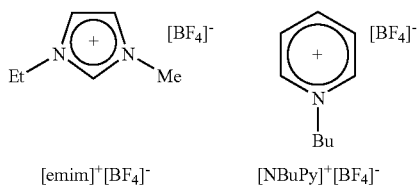

wherein [emim]⁺[BF₄]⁻ stands for 1-ethyl,3-methylimmedazolium tetrafluoroborate, and [NBuPy]⁺[BF₄]⁻ stands for N-butylpyridinium tetrafluoroborate.

Other examples may be 1-Butyl,3-methylimmedazolium (shortened to [bmim]⁺) tetrafluoroborate, its hexafluorophosphate, any of its halides (X), or its triflate [CF3COO]–, according to the following formula:

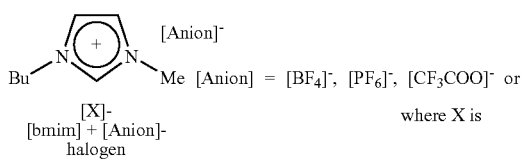

It should be understood that the two alkyl substituents on the immedazolium cycle can be any one independently selected from methyl, ethyl, n- and isopropyl, or any of the possible butyl isomers. Also, any quaternary ammonium cations along with the above anions may be used. Examples are of the formula $[R_xH_yN]^+$, wherein R=methyl, ethyl, propyl, any of the butyl isomers, and x may be 1 or above, and x+y=4. Other anions may be $[PF_6]^-$, $[SbF_6]^-$.

Therefore a further embodiment of this invention is a hydrogenation process using a suitable transition metal hydrogenation catalyst, such as Ni, Co, Cu, Cr, Ru or Rh, but others are also known, dissolved in an ionic liquid which may be contained in a pumparound system to enhance mixing. The hydrogenation feed is then introduced into the reactor system at appropriate temperature and hydrogen partial pressure, and the mixture of hydrogen containing gas and the two liquids is introduced into a hydrogenation reactor. The product from the reactor is then passed on to a settler, optionally after cooling and/or separation of any excess gas, if used. In the settler the organic hydrogenation product typically forms an upper layer that can be withdrawn for further processing, and the ionic liquid comprising the catalyst separates as the bottom layer, which may be recycled to the hydrogenation reactor in the reactor system, optionally after cooling. Alternatively, the reactor itself may be provided with a cooling system. In a further embodiment, the hydrogenation reactor system using the ionic liquid may use a gas lift or a loop reactor, optionally with a cooler as part of the reactor loop.

Such an ionic liquid based hydrogenation reactor system may be used in series with another ionic liquid based hydrogenation reactor system, or with a conventional hydrogenation reactor containing a heterogeneous hydrogenation catalyst. The current invention is applicable to a hydrogenation process using hydrogenation reactors in series, wherein one of the hydrogenation reactors is using a metal hydrogenation catalyst dissolved in an ionic liquid.

In preparation for the hydrogenation phase of the process of the present invention the product from hydroformylation is preferably cooled, passed to a decobalting or demetalling and washing unit (though the cooling can also be performed after demetalling depending on what process for demetalling is selected), filtered to further remove remaining cobalt species. The use of pumice filters is particularly preferred for the removal of cobalt. At this stage the water content of the hydroformylation product is typically between 0.5 and 3 wt % water, which may be dissolved and/or in the form of entrained droplets. Depending on the hydroformylation and/or demetalling process, such water droplets may be very small and be present as a metastable haze that can take 24 hours or more to clear. Typically such a haze represents from 0.1 to 0.4 wt % of free water relative to the organic phase, more typically about 0.2-0.3% wt. These amounts of free water are sufficiently low such that after preheating to the desired entry temperature of the hydrogenation reaction, this free water becomes totally dissolved in the organic phase, and no free water enters the hydrogenation reactor itself. If the hydroformylation is using cobalt catalyst, and the decobalting is using a base, there may also be small amounts of base present in the organic and/or in the free water droplets or haze. The temperature of the product at this stage is typically between 40° C. and 80° C. more typically between 50° C. and 70° C. and especially 60° C. The product is then fed (without any further water addition) to the first hydrogenation reactor where it is hydrogenated over a catalyst bed, preferably a cuprous chrome catalyst at a temperature in the range 170 to 190° C. and a hydrogen pressure of 40 to 60 barg. Alternatively the hydrogenation is performed over a sulphided, alumina supported Co and Mo oxide catalyst at a temperature in the range of 200 to 230° C. and a hydrogen pressure up to 175 barg, or over a sulphided, alumina supported Ni and Mo oxide catalyst at a temperature range of 145 to 185° C. and a hydrogen pressure up to 50 or even as high as 125 barg, wherein the higher pressure is preferred because of suppressing side reaction, an effect that can be noticed up to a pressure of about 125 barg. If the catalyst particle size is sufficiently large to avoid the risk of bed lifting, it is preferred that the product pass in an upward direction through the first hydrogenation reactor since this results in an increased liquid holdup in the reactor and in improved heat transfer to the reactor jacket, if present, or to the reactor shell side in case of a shell and tube type tubular reactor. Adiabatic reactors may also be employed in the hydrogenation process. Multibed chamber reactors may also be employed, and temperature control may be effected by injection of cooled liquid or gas, preferably recycled from a point downstream in the process flow.

Alternatively with low pressure hydroformylation, optionally followed by aldol condensation, the feed for hydrogenation consists primarily of aldehydes, which may contain also a carbon-carbon double bond as a result of the aldolisation, when used, including dehydration. Other compounds present may be alcohols, further aldehyde condensation products such as aldoxanes, acids, esters, ethers, which are possibly cyclic, lactones, hemi-acetals, glycols or cyclic aldols. They may be formed by side reactions such as the Cannizzaro or the Tishchenko reactions during the hydroformylation or the aldolisation process. The feed for hydrogenation may also contain traces of the ligand that is used in the low pressure hydroformylation process. Optionally, the feed for hydrogenation may be distilled before it is passed on to the hydrogenation process, for removing lights and/or heavy by-products and/or the ligand traces or derivatives thereof.

The aldolisation process may be catalysed, and a dilute alkaline solution is typically preferred as the catalyst, more preferably a 2% wt solution of sodium hydroxide or sodium carbonate. The aldolisation product may optionally be passed on to a water wash step to remove traces of the aldolisation catalyst.

Many of these process steps involve the use of water or aqueous solutions, which typically are separated from the organic feed for hydrogenation. In case a distillation step is included, and the hydrogenation feed is produced as a distillate, typically water occurs in the distillation tower overhead, and is separated in the overhead distillate drum. The feed for hydrogenation is therefore typically saturated with water, and may contain entrained water droplets or a water haze due to imperfect separation performance.

The hydrogenation reaction is exothermic and accordingly requires temperature control. Using the cuprous chromite catalyst system, it is preferred that the outlet temperature of the first hydrogenation reactor be no higher than 185° C. since we observe a loss of yield of about 1 to 2% if the temperature exceeds 185° C. The temperature may be controlled by the provision of a cooling jacket around the reactor, in particular if the reactor has a high length/diameter ratio, such as 4 or more.

The product from the first hydrogenation reactor then passes in a line to the second hydrogenation reactor and it is preferred that the line be provided with an inlet for the injection of water and a mixer whereby the water and the product may be mixed to ensure that the water is dissolved and/or entrained in the product. The amount of water injected should be no more than the amount that will bring the total water content to no more than the solubility limit under the conditions of the second reactor. This solubility limit depends on the composition of the stream, the temperature and pressure prevailing in the reactor. Typically we have found that from 0.5 to 3 wt %, especially from 1 to 2 wt % of water based on the weight of the product be injected. We have also found that, in case the upstream demetalling step is acidic, a significantly higher amount of acetals is found in the stream to be hydrogenated. Because these acetals need to be hydrolysed before the resulting aldehyde can be hydrogenated, such high acetal feeds require more water present in the hydrogenation step, such as 4 or 5% by weight in total. In such cases, the injection of extra water in the feed to the second hydrogenation reactor is even more important.

The mixture then passes to the second hydrogenation reactor where it passes through a catalyst bed at a temperature of, for example, 170 to 190° C. at a hydrogen pressure of for example 40 to 200 barg, preferably 40 to 60 barg. In a preferred embodiment the product flows downwardly in the second reactor. It is preferred that a cuprous chrome catalyst also be used in the second reactor and that the outlet temperature of the second reactor be no more than 185° C.

The hydrogenation phase consists of two or more hydrogenation reactors and where more than two reactors are used a cycle such as that described above in relation to the second reactor may be employed with the third and subsequent reactors. Where subsequent reactors are used it is preferred that the cuprous chrome catalyst previously described be used in these subsequent reactors. When three or more reactors are used, regardless of the catalyst selection, several lead reactors may be employed in parallel, and they may have their own individual partial product recycle or a combined partial product recycle. These lead reactors may then be followed by one or a number of further reactors in series, and partial product recycle may be employed over this last series of reactors, or include the lead reactors as well.

Following the last hydrogenation reactor the product passes to a high pressure separator in which unreacted hydrogen may be flashed off and, if desired, recycled to the hydroformylation reactors as is described in our copending U.S. patent application 60/530,805 filed 18 Dec. 2003. It is also possible to recycle some or all of this unreacted hydrogen to the hydrogenation reactors. In this embodiment only a portion of the unreacted hydrogen is passed to the hydroformylation reactors.

The product of hydrogenation following the separation of the hydrogen comprises a mixture of the desired alcohols, olefins and paraffins, alcohol dimers, acetals and traces of aldehydes, acids and formates together with dissolved carbon dioxide and monoxide, and dissolved hydrogen and water. The product may then be cooled and purified further, firstly through a coalescer to remove water, followed by fractional distillation to separate the alcohol from the lower boiling fraction of the mixture and a second distillation step, optionally at a different pressure, to separate the alcohol from the higher boiling fraction. Water and any methanol or other lower alcohols typically will be separated with the lower boiling fraction, and may settle out as a separate phase in the tower overhead system, from where they can be discarded or taken for further use.

The hydrogenation reactors may be vertical tubes, provided with a jacket for temperature control and heat removal. They may be operated in upflow or in downflow mode. In the jacket, water or another suitable cooling medium such as an alkanol, preferably methanol may be circulated using a pumparound system from which hot cooling medium may be withdrawn, and to which cold cooling medium may be supplied. Each reactor may be provided with a so-called conditioner, which is a heat exchanger one side of which is part of the cooling medium circulation, and which on the other side is for conditioning the reactor feed to the appropriate temperature before it passes to the reactor itself. Conditioning of the reactor feed is especially important when a reactor that is not a lead reactor contains relatively fresh and active catalyst, and therefore needs to be operated at start-of-run conditions, this typically requires a lower temperature. The upstream reactor on the other hand, may contain partially deactivated catalyst and therefore needs to be operating at mid-of-run or end-of-run conditions which requires a higher temperature. Feed conditioning can therefore avoid a reactor feed that is too hot for an active catalyst to handle, and can therefore reduce the risk for temperature runaway.

The series of hydrogenation reactors are vertical vessels containing one or more fixed beds of catalyst and are equipped with facilities to distribute the gas and liquid over the catalyst to ensure good contact among the catalyst, liquid and gas phases. The reactors are equipped with facilities to remove the heat of reaction and to control the temperature within the desired range over the life of the catalyst. The reactor dimensions are selected to provide the desired velocity over the beds to give sufficient contacting and to provide adequate residence time to reach the desired conversion of all the components in the feed. Clearly the reactor system will be equipped with that equipment required for startup and shutdown and continuous safety monitoring and response, which need not be described here.

The reactors may utilize a single preheater ahead of the series of reactors or with heat exchange capability between each of the reactors. The conditioning of the temperature between reactors may be useful in the case of reactors running the same type of catalyst, but of different age and activity, and/or in the case of reactors utilizing different catalysts having different optimum operating temperatures.

The reactors may be of several known types, or a combination of types, depending on the method of removing the reaction heat and controlling the temperature. The reaction may be carried out in a bundle of tubes containing catalyst where the heat is removed through the tube walls into circulating coolant which may generate steam in-situ, or externally, or with the hot coolant discarded and replaced with cooler water or cooling medium. The temperature profile in such a reactor is controlled to a desired operating window by virtue of the high heat transfer surface compared to the reactor volume.

At the other end of the spectrum is the purely adiabatic reactor, where the feed is introduced at a temperature where the reaction will initiate, and as the material flows up or down the reactor, the heat is absorbed by the flowing material, raising the temperature as the feed passes through the reactor. Depending on the concentration of the feed, the reactor vessel may be partitioned into separate catalyst beds where the inlet temperature to each bed is readjusted such that the temperature rise does not exceed the desired maximum temperature. The temperature adjustment may be done by conventional heat exchangers or by the injection of cooled and partially converted reactor product or cold hydrogen.

The adiabatic reactor may have its overall temperature rise limited by dilution of the feed by a suitable diluent, the most preferable being the recycle of substantially converted product at a ratio to the feed between about 2.8 and 10, depending on the feed concentration and the desired exotherm. Preheating of the reactor feed may not be needed for routine operation; only the mixed feed temperature conditioning may be necessary at the inlet to the catalyst bed.

The reactors may be equipped with external jackets in which the cooling medium is circulated integrally with the reactor feed conditioner. The amount of heat transferred across the reactor wall into this cooling circuit is dependent on the reactor diameter, and will be important for reactors of smaller diameter, such as 0.5 meter or less. When the coolant flows in a direction counter to the process flow, and the radial heat transfer is substantial, this type of reactor approaches what is known in the art as autothermal reactor status. This particular design has advantages in energy efficiency.

Any of these reactor types are sufficient and may be used uniformly or mixed considering the differences in efficiency, controllability, safety, and initial investment.

The present invention is illustrated by reference to the accompanying schematic FIG. 1, which shows a hydroformylation reactor (101), which may be a series of reactors, a catalyst removal system including a wash tower (102), a hydrogenation feed preheat system followed by a mixer (103), a first hydrogenation reactor (104), an injection point followed by a second mixer (105), a second hydrogenation reactor (106) and possibly more hydrogenation reactors (107).

Olefin and synthesis gas are fed to the hydroformylation reactor (101) at (1) and water is injected at (2); following hydroformylation the product (3) is fed to a catalyst removal step and then to wash tower (102) into which water (4) is introduced. The demetalled and washed product (5) passes at (6) into the mixer (103) and then as (7) to the first hydrogenation reactor (104). After the first hydrogenation the material (8) passes to the injection point where water (9) is injected into the material and the combination passes to the mixer (105). The mixed product (10) then passes to the second hydrogenation reactor (106) from which it exits as product (11) which may be subject to further hydrogenation (107) and/or purification.

It will be appreciated that FIG. 1 is a schematic illustration of the essential aspects of the invention and more detail concerning the operation of the hydroformylation section can be obtained from our above-mentioned copending U.S. patent application 60/530,805 filed 18 Dec. 2003.

EXAMPLES

By way of example, a hydrogenation feed produced by the hydroformylation of octenes using the high pressure cobalt process, and with the composition as given in Table 1, was hydrogenated in two different ways. The experimental setup comprised a pumice filter followed by a series of 5 upflow hydrogenation reactors of equal volume and of a total catalyst volume of 550 ml. The rate of feed to hydrogenation was 600 ml/h, and hydrogen feed rate was 100 normal liter per hour. Total pressure was 55 barg, and the reactors were all kept isothermal at 190 deg C. Water was injected into the feed to the first hydrogenation reactor in order to simulate commercial conditions of water saturated feed to the first hydrogenation reactor. In the first comparative example, no water was injected into the feed to the second hydrogenation reactor. In the example according to the invention, additional water was injected in the feed to the second hydrogenation reactor. Table 1 gives the product analyses for the two examples, and the effect on better acetal reduction can be observed.

TABLE 1

| | Feed | Example 1 (Comparative) | Example 2 (Invention) |
|---|---|---|---|
| Water on hydrogenation feed | | | |
| To lead hydrogenation reactor | | 1.96 wt % | 2.30 wt % |
| To second hydrogenation reactor | | — | 2.31 wt % |
| Stream composition (wt % by GC) | | | |
| Methanol | 0 | 0.44 | 0.23 |
| Olefins + Paraffins | 1.56 | 1.53 | 1.50 |
| Aldehydes + Alcohols + Formate esters | 56.86 | 83.13 | 84.16 |
| Acetals | 28.48 | 3.76 | 2.46 |
| Other heavies | 13.10 | 11.14 | 11.64 |
| Other analytics | | | |
| Carbonyl number (mg KOH/g) | 82.2 | 4.99 | 2.7 |
| Cold Sap number (mg KOH/g) | 38.5 | 1.61 | 1.24 |

The invention claimed is:

1. A process for the production of alcohols comprising:
   hydroformylating a feedstock comprising at least one olefin in a hydroformylation reactor to form a hydroformylation product comprising an organic phase;
   hydrogenating the hydroformylation product in a series of at least two reactors to produce an alcohol, wherein at least one of the hydrogenation reactors comprises a catalyst that can be poisoned by sulphur, and
   passing water into the product of the first hydrogenation reactor before the product is passed into the second hydrogenation reactor, wherein substantially all of the water present is dissolved in the organic phase in the second hydrogenation reactor and wherein the feed to the first hydrogenation reactor has a sulphur content of below 1 ppm by weight and a chlorine content of below 1 ppm by weight.

2. A process according to claim 1 comprising adding water to the hydroformylation reactor and to the second hydrogenation reactor, but wherein no further water is added in the first hydrogenation reactor.

3. The process according to claim 1 wherein the process further comprises (a) demetalling the hydroformylation product and/or (b) washing the hydroformylation product, and wherein water from demetalling or washing passes into the first hydrogenation reactor, and wherein substantially all of the water present in the demetalled and/or washed hydroformylation product passed into the first hydrogenation reactor is dissolved in the organic phase in the first hydrogenation reactor.

4. The process according to claim 1 wherein substantially all of the water present in the hydroformylation product passed into the first hydrogenation reactor is dissolved in the organic phase in the first hydrogenation reactor.

5. The process according to claim 1 wherein the sulphur content of the feed to the first hydrogenation reactor is below 0.1 wt ppm.

6. The process according to claim 1 wherein the chlorine content of the feed to the first hydrogenation reactor is below 0.1 wt ppm.

7. The process according to claim 1 wherein the feedstock to the hydroformylation reactor has a sulphur content below 1 wt ppm.

8. The process according to claim 1 wherein the feedstock to the hydroformylation reactor has a chlorine content below 1 wt ppm.

9. The process according to claim 1 wherein the feedstock comprises one or more $C_5$ to $C_{14}$ olefins and the alcohol is an $C_6$ to $C_{15}$ alcohol.

10. The process according to claim 1 wherein the hydroformylation reactor is operated at elevated temperatures and pressures using a cobalt catalyst.

11. The process according to claim 10 comprising removing cobalt species from the hydroformylation product prior to hydrogenation in the first hydrogenation reactor.

12. The process according to claim 10 comprising treating the hydroformylation product before hydrogenation so that the cobalt content is below 2 wt ppm.

13. The process according to claim 1 comprising operating the hydroformylation reactor at pressures of from 50 to 350 barg and temperatures of from 165 to 185° C.

14. The process according to claim 1 wherein the hydroformylation reaction is performed in a series of at least two reactors.

15. The process according to claim 1 comprising controlling the gas composition in the hydroformylation reactor(s) by controlling the amount and/or composition of the recycle of unreacted gases from hydroformylation step.

16. The process according to claim 14 comprising recycling hydrogen from one or more the hydrogenation reactors to the second (and/or any subsequent) hydroformylation reactors.

17. The process according to claim 14 comprising a series of at least three hydroformylation reactors, the process comprising recycling a hydrogen-rich gas, the hydrogen rich gas comprising recycle gas from one or more hydroformylation reactors and/or one or more hydrogenation reactors.

18. The process according to claim 1 wherein the hydroformylation catalyst comprises a cobalt catalyst and cobalt catalyst species are removed by passing a base into the hydroformylation reaction product in a decobalter vessel positioned downstream of the final hydroformylation reactor.

19. The process according to claim 1 further comprising aldolising at least a portion of an aldehyde product of the hydroformylation step and hydrogenating at least a portion of the aldolisation product.

20. The process according to claim 19 comprising passing water carried over from the aldolisation reactor into the first hydrogenation reactor, the amount of water carried over being such that all the water present in the first hydrogenation reactor is dissolved in the organic phase to be hydrogenated in the first hydrogenation reactor.

21. The process according to claim 20 comprising adding water to the feed to second hydrogenation reactor, the amount of water added being such that all the water present in the second hydrogenation reactor is dissolved in the organic phase.

22. The process according to claim 19 wherein the feedstock for the hydroformylation reactor comprises one or more C2 to C4 olefins.

23. The process according to claim 22 wherein the hydroformylation catalyst comprises a rhodium catalyst.

24. The process according to claim 22 wherein the hydroformylation catalyst comprises a phosphorus ligand.

25. The process according to claim 24 wherein the phosphorus ligand is triphenylphosphine.

26. The process according to claim 24 wherein the phosphorus ligand is an organic phosphite.

27. The process according to claim 26 wherein the organic phosphite is 6,6'-[[3,3',5,5'-tetrakis(1,1-dimethylethyl)-1,1'-biphenyl]-2,2'-diyl] bis(oxy)] bis-dibenzo[d,f][1,3,2]-dioxaphosphepin.

28. The process according to claim 22 wherein the alcohol comprises a C8 alcohol and wherein the olefin comprises propylene.

29. The process according to claim 22 wherein the alcohol comprises a C9 alcohol and wherein the olefin comprises ethylene.

30. The process according to claim 22 wherein the alcohol comprises a C10 alcohol or a C10 alcohol mixture and the olefin comprises butene or a butene mixture.

31. The process according to claim 1 wherein the hydrogenation catalyst is a copper chrome catalyst.

32. The process according to claim 31 wherein the hydrogenation catalyst contains from 20% to 40% by weight of each of copper and chromium based on the total weight of hydrogenation catalyst including any support.

33. The process according to claim 1 wherein the hydrogenation catalyst is selected from the group consisting of a monometallic catalyst composition on a solid support, a bimetallic catalyst composition on a solid support and a trimetallic catalyst composition on a solid support.

34. The process according to claim 33 wherein the support is selected from the group consisting of alumina, silica-alumina and a carbonaceous support.

35. The process according to claim 34 wherein the catalyst further comprises an acidity modifier.

36. The process according to claim 35 wherein the acidity modifier comprises a member selected from Group IA and IIA of the Periodic Table of the Elements.

37. The process according to claim 36 wherein the acidity modifier comprises a member selected from the group consisting of magnesium, sodium, potassium, compounds containing magnesium, compounds containing sodium and compounds containing potassium.

38. The process according to claim 1 wherein the hydrogenation catalyst comprises a transition metal and is dissolved in an ionic liquid.

39. The process according to claim 38 wherein the transition metal is at least one member selected from the group consisting of nickel, cobalt, copper, palladium, chromium, ruthenium, rhodium and mixtures of at least two thereof.

40. The process according to claim 38 wherein the ionic liquid comprises in combination a first component selected from the group consisting of [BF4]−, halide anions, [PF6]−,

[CF3COO]−, and [SbF6]−, and a second component selected from the group consisting of [emim]+, [bmim]+, and any other disubstituted immedazolium, the substituents being selected from the group consisting of C1-C4 alkyl, [NBuPy]+ and other suitable alkylammonium cations.

41. The process according to claim 1 wherein the product from the first hydrogenation reactor passes in a line to the second hydrogenation reactor and water is injected into the line and the mixture passes to a mixer whereby the water and the product are mixed so that the water is entrained with the product, and the mixture is then passed to the second hydrogenation reactor where it passes through a catalyst bed at a temperature of 170 to 190° C. at a hydrogen pressure of 40 to 200 barg.

42. The process according to claim 41 wherein from 1 to 2 wt % of water based on the weight of organic material is injected.

43. A mixture of olefins comprising C5 to C13 olefins comprising at most 90 mol % of normal olefins, the olefin mixture containing below 1 ppm sulphur by weight, and below 1 ppm chlorine by weight.

44. The mixture according to claim 43 comprising at least 3 isomers with different skeletal structures.

45. The olefin mixture according to claim 44 wherein more than 50 wt % of the mixture comprises C8 olefins.

46. A hydrogenation feed stream comprising C6-C15 aldehydes, the hydrogenation feed stream containing no more than 1 ppm sulphur and no more than 1 ppm chlorine.

47. The hydrogenation feed stream according to claim 46 comprising an aldehyde containing nine carbon atoms.

* * * * *